United States Patent [19]

Blair et al.

[11] 4,330,626

[45] May 18, 1982

[54] METHOD OF PREPARING HIGH-ACTIVITY, LOW-BACTERIA, UREASE ENZYME

[75] Inventors: Henry E. Blair, Barnstable; Stanley E. Charm, Newton; Richard P. Crowley, Boston, all of Mass.

[73] Assignee: The Enzyme Center, Inc., Boston, Mass.

[21] Appl. No.: 131,742

[22] Filed: Mar. 19, 1980

[51] Int. Cl.$^3$ .................. C12N 13/00; C12N 9/80
[52] U.S. Cl. .................. 435/173; 435/228; 422/22
[58] Field of Search ............. 435/173, 228; 422/22, 422/23

[56] References Cited

U.S. PATENT DOCUMENTS 3,249,513  5/1966  Babson ........................ 435/228
4,193,845  3/1980  Kaetsu et al. ............... 435/173 X

*Primary Examiner*—Lionel M. Shapiro
*Attorney, Agent, or Firm*—Richard P. Crowley

[57] ABSTRACT

In a method of preparing the enzyme, urease, from jack beans, wherein the jack beans are reduced to a fine particle size and the fine particles so reduced constitute urease, the fine jack-bean particles thereafter irradiated for a period of time, the irradiated jack beans then recovered and employed as a source of urease enzyme, the improvement which comprises: irradiating the whole jack beans prior to any size reduction of the seeds of the jack beans, to provide a urease derived from the white seeds of the irradiated whole jack beans having an improved activity level.

6 Claims, No Drawings

METHOD OF PREPARING HIGH-ACTIVITY, LOW-BACTERIA, UREASE ENZYME

BACKGROUND OF THE INVENTION

Jack beans are derived from a bulky leguminous plant also known as canavalia ensiformis, which plant is grown in tropical regions. The seed of the jack bean encased in the jack-bean hull or shell is a source of the enzyme, urease, also known as urea amidohydrolase. The enzyme, urease, derived from the jack-bean plant is commercially sold in varying forms of purity for use; for example, in home-permanent hair kits, as well as an active enzyme employed in various clinical diagnostic kits. The enzyme, urease, is sold in finepowder particulate form in accordance with specifications relating to bacterial examination and enzyme activity. Enzyme activity may be defined in one test in terms of the micromoles of ammonia liberated per minute at 25° C. at a pH of 7.6 under certain confined conditions (see, for example, Sumner, J. B., Urease, *Methods in Enzymology* 2, p. 378 (1955), and Gorin, G. and Chin, C. C., *Anal. Biochem.*, 17, 49–59 (1966). For example, urease might be sold with a contaminant level of ammonia of less than 0.001 micrograms per unit. Urease also is prepared and sold in connection with a specific activity of greater, for example, than 170 u/mg protein. The urease also should have a microbiological specification typically less than 1000 units per gram of nonpropagating, nonpathogenic bacteria.

The present technique of preparing urease from jack beans comprises the grinding of the seeds of the jack beans comprising the crude urease into a fine particle size, such as a ground product which has a maximum of 0.1% on a 60-mesh sieve with ethanol. Thereafter, the finely-divided jack-bean seeds are subjected to irradiation, in order to reduce the bacteria or microbiological contamination to an acceptable level, such as by irradiation of the powder through exposure to gamma radiation of a cobalt-60 source or by a Van der Graaf accelerator or some other gamma-irradiation techniques or high electron-voltage techniques. In this process, microorganisms contaminating the outer hull surface and black beans; that is, beans which are highly contaminated with bacteria or pathogens, are ground into and become part of the ground or fine-particle urease prior to irradiation. This technique raises the bacterial and pathogenic level of the material to be irradiated. By such technique, crude urease is obtained generally having an activity of greater than about 200 to 225 (mg NH$_3$/g sample/5 min at 25° C.) and a nonpathogenic contamination of less than 1000.

SUMMARY OF THE INVENTION

Our invention relates to a new and improved low-bacterial-level, high-activity urease and to a method of preparing a high-activity, low-bacterial-level urease.

It has been discovered that surprising and unexpected results are achieved when, in the process of preparing urease, the whole jack bean; that is, the hull and the seed together, are irradiated prior to any reducing operation which reduces the size of the whole jack bean. It has been discovered that the irradiation of the whole jack bean, wherein the hull or shell comprises, for example, from 14% to 18% by weight of the jack bean, provides a simple, effective process, wherein the urease produced from the subsequently ground or reduced irradiated jack bean is low in microbiological contamination.

Our process produces a urease having higher specific activity, than where the prior-art techniques are employed. Thus, by a simple and effective irradiation of the whole jack bean, the advantage of less specific inactivity of the resulting urease is provided, with lower loss of the urease material.

Although not wishing to be bound by any particular theory as to the method of operation or function of our invention, it is believed that the irradiation of the whole jack bean and the results achieved thereby may be associated with the rapid rate of surface oxidation or chemical reaction, when the seed of the bean has been ground to fine particle size, so that irradiation of the white seed within the hull provides for reduced opportunity for chemical reaction or oxidation and, therefore, provides for less specific inactivity.

In our method, the whole bean, after harvesting from the plant, is irradiated, such as by exposure to any desired level of gamma or other irradiation, but typically, for example, gamma irradiation of from about 0.1 to 5.0 megarads, but more typically from 0.30 to 2.5 megarads, such as, for example, about 0.5 to 1.8 megarads. If desired, before or after irradiation of the whole bean, any contaminated or black beans may be removed from the mass of beans, so as to reduce the bacterial contamination even to lower levels, prior to size reduction of the irradiated beans. After irradiation, the white seeds are ground, classified to remove hulls and then are employed as a source of crude urease or, if desired, are subjected to refining techniques, to provide a defined urease enzyme, depending upon the desired end use.

For the purpose of illustration only, it being recognized that persons skilled in the art may make various changes and modifications in our invention, without departing from the spirit and scope of our invention, our invention will be illustrated by certain comparative examples.

DESCRIPTION OF THE EMBODIMENTS

EXAMPLE

Whole jack-bean samples were ground and screened to pass an 80-mesh sieve and then indicated with gamma-ray irradiation from a Cobalt-60 source, and the specific activity of the irradiated samples in milligrams of ammonia per gram of sample per 5 minutes (mg NH$_3$/gm/5 min) was determined and the loss of activity due to the irradiation, with the results being shown in Table I.

A whole jack-bean sample was irradiated in the same manner with a minimum of 0.78 megarads to a maximum of 2.1 megarads of gamma irradiation and, thereafter, ground and screened to the same size as the ground jack beans. The specific activity of the ground jack beans was then determined, with the results being set forth in Table I.

TABLE I

| Sample | Activity (mg NH$_3$/gm/5 min) | Gamma Dose (megarads) | % Loss in Activity |
|---|---|---|---|
| | | Irradiation of Ground Jack Beans | |
| Control | 216.5 | 0 | — |
| 1 | 198.9 | .7 | 8.1 |
| 2 | 181.9 | 1.0 | 16.0 |
| 3 | 177.7 | 1.3 | 17.9 |
| 4 | 171.3 | 1.7 | 20.9 |
| | | Irradiation of Whole Jack Beans | |

TABLE I-continued

| Sample | Activity (mg NH₃/gm/5 min) | Gamma Dose (megarads) | % Loss in Activity |
|---|---|---|---|
| Control | 204.9 | 0 | — |
| A | 191.9 | .78 to 2.1 | 6.6 |

The irradiation of the whole jack bean, prior to grinding and screening as in our process, provided for a significantly lower loss in specific activity; that is, a loss of about 6.6% versus an average loss by the prior-art technique of 17.4%. The level of specific activity should be less than 300; for example, 200–250, and typically more than 170 (mg NH₃/gm/5 min at 25° C.).

What we claim is:

1. In a method of preparing the enzyme, urease, from jack beans, wherein the jack beans are reduced to a fine particle size and the fine jack-bean particles thereafter irradiated by gamma irradiation for a period of time, the irradiated jack beans then recovered and employed as a source of urease enzyme, the improvement which comprises:

irradiating the whole jack beans with gamma irradiation prior to size reduction of the jack beans, to provide a urease having lower loss of activity than where the jack beans are first reduced in size and then irradiated.

2. The method of claim 1 wherein the amount of gamma irradiation is from about 0.1 to 5.0 megarads.

3. The method of claim 1 wherein the specific activity of the urease is from about 170 to 300 based on the milligrams of ammonia liberated per gram of urease per 5 minutes at 25° C.

4. The method of claim 1 wherein the jack beans, having high levels of microbiological contamination, are removed prior to the size reduction of the jack beans.

5. The method of claim 1 wherein the irradiated jack beans are ground into a particle size of less than about 60 mesh.

6. In a method of preparing the enzyme, urease, from jack beans, wherein the jack beans are reduced to a fine particle size and the fine jack-bean particles thereafter irradiated by gamma irradiation for a period of time, the irradiated jack beans then recovered and employed as a source of urease enzyme, the improvement which comprises:

irradiating the whole jack beans with from about 0.3 to 2.5 megarads of gamma-ray irradiation prior to size reduction of the jack beans to less than about 60 mesh, to provide a urease having a specific activity of from about 170 to 300 milligrams of ammonia liberated per gram of urease per 5 minutes at 25° C.

* * * * *